(12) United States Patent
Calton et al.

(10) Patent No.: US 6,284,232 B1
(45) Date of Patent: Sep. 4, 2001

(54) ODOR REDUCING COMPOSITIONS

(75) Inventors: Gary J. Calton, Elkridge, MD (US); John B. Cook, Phoenixville, PA (US)

(73) Assignee: OdorPro, Inc., Elkridge, MA (US)

( * ) Notice: Subject to any disclaimer, the term of this patent is extended or adjusted under 35 U.S.C. 154(b) by 0 days.

(21) Appl. No.: 09/312,186

(22) Filed: May 14, 1999

(51) Int. Cl.[7] .................................................. A61L 9/00
(52) U.S. Cl. .................... 424/76.1; 424/76.2; 424/75.21; 424/76.4; 424/76.6; 424/76.8
(58) Field of Search .................... 424/76.1, 76.2, 424/76.21, 76.22, 76.4, 76.6, 76.8

(56) References Cited

U.S. PATENT DOCUMENTS 6,068,665 * 5/2000 Calton et al. ............................ 8/137
6,152,150 * 11/2000 Cook et al. .............................. 134/7

* cited by examiner

*Primary Examiner*—Shelley A. Dodson

(57) ABSTRACT

Synergistic mixtures of a zeolite and an imide provide superior relief from objectionable odors. The compostions are especially effective to remove the odor of animal wastes or fluids. The mixture may be sprinkled on dogs, dog bedding, horse stalls, animal vomit, urine deposits, fish remains, fish juices and the like. The zeolite/imide mixture will also remove odors from carpets, clothes, hands or other body parts, cloth and plastic items.

27 Claims, No Drawings

ODOR REDUCING COMPOSITIONS

FIELD OF THE INVENTION

This invention relates to novel zeolite/imide compositions and the method of use thereof for the reduction of odors.

BACKGROUND OF THE INVENTION

Odor control has been a significant problem for which there are very few solutions. Ammonia and amines are by far the most objectionable odor. Their volatility makes them quite noticeable when even small amounts are released.

Odor control is of particular interest in the area of human and animal waste disposal. Generally, disposal of waste product from small animals and pets is accomplished by the use of animal litter capable of absorbing waste products. However, conventional litter materials fail to adequately suppress odors.

Odor control is also of interest for products such as foods, clothing, personal care products, foul-smell lagoons, holding tanks and industrial wastes.

Zeolites and imides have been used for odor control. For example, U.S. Pat. No. 5,013,335 discloses the use of zeolites for control of ammonia odor.

U.S. Pat. Nos. 3,776,118 and 3,898,324 teaches inhibiting the formation of odors from poultry farms. These patents disclose the use of a dried fine powder of zeolite with a course powder of crystalline ferrous sulfate hepta-hydrate as a stabilizer. The deodorizing agent disclosed in these patents is the sulfate hepta-hydrate.

In U.S. Pat. No. 4,256,728, zeolites are disclosed for use in a deodorization method. In this patent, however, the zeolite acts as a support for an acid, such acid serving as the deodorization agent.

U.S. Pat. No. 4,059,545 discloses the use of clinoptilolite in the ammonia exchanged form and treated with a dilute solution of a strong acid to act as an absorbent for acid gases.

U.S. Pat. No. 4,437,429 discloses the reduction of ammonia odor from animal litter containing clay by the addition an effective amount of hydrated zeolite. No appreciable odor from wastes was obtained when 10–60% of the total clay/zeolite litter was zeolite.

In U.S. Pat. Nos. 5,833,972 and 5,869,027 the use of an imide for controlling an odor is disclosed.

SUMMARY OF THE INVENTION

It has now been discovered that the combination of zeolite and an imide acts synergistically to provide superior control of odors when compared to the use of either ingredient alone. Zeolite/imide compositions in accordance with the invention are especially effective against odor causing amines and ammonia. In addition, the novel compositions of the invention are effective to control odors not known to be odoriferous as a result of amines or ammonia, or not heretofore known to be removed by either of zeolite or an imide alone.

Accordingly, it is an advantage of this invention to provide novel zeolite/imide compositions useful for reducing or eliminating odors. Another advantage of this invention is to provide a method of using the novel compositions to remove or eliminate odors, especially those odors associated with human and animal waste products.

DETAILED DESCRIPTION OF THE EMBODIMENTS

Odor reducing compositions in accordance with the invention comprise a mixture of a zeolite and an imide. The zeolite and imide components are present in the mixture in an amount sufficient to reduce or eliminate odors. In general, the ratio of zeolite to imide present in the mixture ranges from about 1:1 to about 99.9:0.1.

Zeolites useful to prepare mixtures in accordance with the present invention include naturally occurring or synthetic zeolites. Zeolites are characterized by an aluminosilicate tetrahedral framework, and have ion exchangeable large cations and loosely held water molecules permitting reversible dehydration. The general formula for a zeolite is as follows: $MO.Al_2O_3.nSiO_2.xH_2O$, where M is Na, K, Ca, Sr or Ba and n and x are integers.

The oxygen atoms in the framework of the zeolite are each shared by two tetrahedrons, thus, the (Si, Al):O ratio is exactly 1:2. The amount of large cations present is dependent on the aluminum to silicon ratio and the formal charge of these large cations. The large cations, which are coordinated by framework oxygens and water molecules, reside in large cavities in the crystal structure. These cavities and channels may even permit the selective passage of organic molecules.

A partial listing of natural zeolites is given in Table 1.

TABLE 1

| Group | Name | Formula |
| --- | --- | --- |
| Analcime | Analcime | $Na(Al_{16}Si_{32}O_{96}).16H_2O$ |
|  | Wairakite | $Ca_{16}(Al_{16}Si_{32}O_{96}).16H_2O$ |
|  | Pollucite | $Cs_{32}(Al_{16}Si_{32}O_{96}).16H_2O$ |
| Sodalite | Sodalite | $Na_6(Al_6Si_6O_{24}).2NaCl$ |
|  | Faujasite | $(Na_2, Ca, Mg)_{29}((Al_{58}Si_{134}O_{384}).240H_2O$ |
| Chabazite | Chabazite | $Ca_6(Al_{12}Si_{24}O_{72}).40H_2O$ |
|  | Gmelinite | $(Na_2, Ca)_4[Al_8Si_{16}O_{48}].24H_2O$ |
|  | Erionite | $(Na_2Ca)_{3.5}K_2[Al_9Si_{27}O_{72}].27H_2O$ |
|  | Offretite | $(Ca, Mg)_{1.5}K[Al_4Si_{14}O_{36}].14H_2O$ |
|  | Levyne | $Ca_9(Al_{18}Si_{36}O_{108}).50H_2O$ |
| Natrolite | Natrolite | $Na_{16}(Al_{16}Si_{24}O_{80}).16H_2O$ |
|  | Scolecite | $Ca_{16}(Al_{16}Si_{24}O_{80}).16H_2O$ |
|  | Mesolite | $Na_{16}Ca_{16}(Al_{16}Si_{24}O_{80}).64H_2O$ |
|  | Edingtonite | $Ba_2(Al_4Si_6O_{20}).8H_2O$ |
|  | Thomsonite | $Na_4Ca_8(Al_{20}Si_{20}O_{80}).24H_2O$ |
|  | Gonnardite | $Na_{6.42}, K_{0.01}, Ca_{1.5}Al_{9.22}OSi_{110.43}O_{40}.12.37H_2O$ |
| Phillipsite | Phillipsite | $K_2(Ca, Na_2)_2(Al_6Si_{10}O_{32}).12H_2O$ |
|  | Harmontome | $Ba_2(Al_4Si_{12}O32).12H_2O$ |
|  | Gismondine | $Ca_4(Al_8Si_8O_3).16H_2O$ |
|  | Garronite | $(NaCa_2)_5(Al_6Si_{10}O_{32}).13H_2O$ |
| Mordenite | Mordenite | $Na_8(Al_8Si_{40}O_{96}).24H_2O$ |
|  | Diachiardite | $Na_5(Al_5Si_{19}O_{48}).12H_2O$ |
| Other | Clinoptilolite | $Na_6(Al_6Si_{30}O72).72H_2O$ |
|  | Heulandite | $Ca_4(Al_8Si_{28}O_{72}).24H_2O$ |
|  | Brewsterite | $(Sr, Ba)_2(Al_4Si_{12}O_{32}).10H_2O$ |
|  | Epistilbite | $Ca_3(Al_6Si_{18}O_{48}).16H_2O$ |
|  | Stilbite | $Na_4Ca_8(Al_{20}Si_{52}O_{144}).56H_2O$ |
|  | Yugawaralite | $Ca_2(Al_4Si_{12}O_{32}).8H_2O$ |
|  | Laumontite | $Ca_4(Al_8Si_{16}O_{48}).16H_2O$ |
|  | Ferrierite | $Na_2Mg_2(Al_6Si_{30}O_{72}).18H_2O$ |
|  | Paulingite | $(K_2, Ca, Na_2)_{76}[Al_{152}Si_{520}O_{1344}]-7H_2O$ |

Prior art techniques have resulted in the formation of a great variety of synthetic zeolites. These zeolites have come to be designated by letter or other convenient symbols, as illustrated by zeolite A (U.S. Pat. No. 2,882,243), zeolite X (U.S. Pat. No. 2,882,244), zeolite Y (U.S. Pat. No. 3,130, 007), zeolite ZK-5 (U.S. Pat. No. 3,247,195), zeolite ZK-4 (U.S. Pat. No. 3,314,752), zeolite ZSM-5 (U.S. Pat. No. 3,702,886), zeolite ZSM-1 (U.S. Pat. No. 3,709,979), zeolite ZSM-12 (U.S. Pat. No. 3,832,449), zeolite ZSM-20 (U.S. Pat. No. 3,972,983), zeolite ZSM-23 (U.S. Pat. No. 4,075, 842), zeolite ZSM-35 (U.S. Pat. No. 4,016,245), zeolite ZSM-38 (U.S. Pat. No. 4,046,859), to name a few, each reference being incorporated herein by reference.

While any zeolite may be used to prepare the odor controlling mixtures of the invention, preferred zeolites include clinoptilolite, chabazite, mordenite, Y, 4A, 5A, P, ZSM-5 and Silicalite in which the silica alumina ratio was varied between 2 and 600. It is within the scope of this invention to use calcined zeolites such as 4A, Y, Mordenite, Silicalite or combinations thereof.

The zeolite is present in the mixture in the form of particles having a diameter ranging from about 2 mm or less. Preferably the particles have a diameter ranging from about 0.5 to 2 mm. In a more preferred embodiment, the zeolite particles have a particle size of 0.044 to 0.5 mm in diameter. In a still more preferred embodiment, the particle size of the zeolite particles is less than about 0.044 mm in diameter.

Any imide may be used to prepare the odor controlling mixture of the invention, however, a preferred imide is disclosed in U.S. Pat. No. 5,833,972 and U.S. Pat. No. 5,869,027, said references herein incorporated by reference. In the most preferred embodiment, the imide is a polyamide selected from the group consisting of polysuccinimide, polyglutarimide and copolymers and terpolymers of thereof, and combinations thereof.

The imide is present in the mixture in an amount up to 50% by weight of the total odor controlling mixture. Preferably, the imide is present in the mixture in an amount ranging from about 0.05 to about 10% by weight of the total mixture. Most preferably, the mixture comprises an imide content of about 0.1 to about 5% by weight of the total mixture.

Compositions are prepared by mixing a zeolite, or mixtures thereof, with an imide, or mixtures thereof. The odor reducing compositions may be used in the form of a powder or a solution depending on such factors as solubility of the imide and the addition of dispersants to maintain the zeolite, or mixtures thereof, in supension. Preferably, the odor reducing compositions are used in the form of a powder.

The method of using the zeolite/imide compositions to control odors comprises contacting an odor with the odor-reducing mixture in an amount sufficient to reduce or eliminate the odor. The mixture may be applied by spraying or spreading as powders, or held by means of binders. Alternatively, the zeolite/imide maybe retained on a floating object to allow the composition to be held on a desired surface. The floating object may be a film or a particle, especially biodegradable particles such as those obtained from corn, rice, wheat, cellulose, soy and the like.

Numerous applications of the invention compositions are envisioned. The zeolite/imide compositions can be dispersed as a powder on particles, such as clay or other absorbent inorganic or organic materials, for use in controlling odors in animal litter. The zeolite/imide compositions may also be incorporated into or on the bedding, clothes or carpeting contaminated by animal wastes to control the odor from animal waste products, may be mixed with animal litter to control odors emitted from animal waste products. The odor reducing compositions can be deposited directly on solid or liquid waste, especially urine, in kennels, stalls, barns, pens and yard space housing animals including fowl, pigs and cattle to reduce or eliminate ammonia and amine levels and effect the release of other objectionable odors not caused by these sources.

The zeolite/imide compositions of the invention may also be incorporated into personal care products such as diapers, both adult and infant, incontinent pads, surgical sponges and dressings, surgical pads, catamenial devices such as sanitary napkins, shields, liners, tampons to control human waste products normally deposited on such products. The zeolite/imide compositions can also be used to control food odors such as onions, fish and garlic. In this case, the composition may be deposited as powders on trays, bags, containers and cooking surfaces, utensils and or clothing to remove the offending odor. Such trays, bags or containers may be made of paper, plastic, wood, metal or ceramics.

The zeolite/imide compositions can also be incorporated in holding facilities, including foul smelling lagoons, such as those containing animal wastes, or tanks, especially those used for holding human, pig, cattle or other farm wastes, and more especially when the zeolite/imide compositions are in the form of films or incorporated in films to prevent escape of odors. They can also be used to reduce the odor from sulfite liquor waste ponds or other similar industrial waste treatment facilities. Such reduction can be achieved by mixing the zeolite/imide compositions with the waste or by depositing the composition on an inert or biodegradable object and allowing the object to come into contact with the waste at the surface, in the body of the waste or on the bottom of the lagoon, holding tank or pond.

Further, such zeolite/imide compositions may be useful in removing ammonia or amines containing body wastes from the blood stream, by immobilizing or attaching to a blood non-reactive material, provided that any reactive material is non-toxic.

In order to further illustrate the present invention and the advantages thereof, the following examples are given. It is understood that the examples are intended only as illustrative and are not intended to be limiting in nature.

EXAMPLE 1

Removal of Cat Urine

A mixture of clinoptilolite and polysuccinimide (10:1, 2 tablespoons) was mixed with with Tom Cat urine in a 2 inch radius cup with ¼ inch of urine in it, stirred for 5 seconds and the cup was tested by two volunteers for odor. The odor was completely eliminated within 15 seconds.

A sick cat urinated on a new sofa with a urethane cushion the covering fabric which had been pre-treated with a stain guard. The area of the covering fabric where the cat urinated was covered with a mixture of clinoptilolite and polysuccinimide (97.75:2.25) and the odor was completely eliminated. The urethane cushion was also treated for odor with the same results. No odor returned when the mixture was vacuumed.

EXAMPLE 2

Removal of Dried Puppy Urine on Carpet

A 10 day old urine spot on carpet was lightly misted with water and covered with a zeolite/imide mixture of clinoptilolite and polysuccinimide (97.75:2.25) and was allowed to dry. The spot was vacuumed approximately 10 hours later. The odor was completely eliminated.

EXAMPLE 3

Incorporation into Cat Litter

A zeolite P/polysuccinimide mixture (75:25) was lightly sprinkled on the surface of the cat litter box. The odor associated with the box was immediately removed. The box was left undisturbed by humans for the next five days after which it changed it even though it had no odor. In a control period, the cat litter box was required to be changed twice daily to satisfactorily control the objectionable cat odor.

EXAMPLE 4

Removal of Dog Odor

A Great Dane (female) was dusted lightly with a clinoptilolite/polysuccinimide mixture (90:10) and the odor was immediately eliminated. The dog remained odor free for at least one week.

EXAMPLE 5

Removal of Horse Urine

A cup of a mixture a clinoptilolite/polysuccinimide mixture (95:5) was spread around the central area of a horse stall containing a mature (5 year old) stallion. Manure was removed daily and no urine odor was noted in the stall. Previously the urine odor (mainly ammonia) was overpowering to the horse trainer.

EXAMPLE 6

Removal of Odor in Dog Bedding

A cushion used by two dogs for bedding was sprinkled with a zeolite P/polysuccinimide mixture (95:5) and the odor was removed. The concrete beneath the bedding was sprinkled with the zeolite/imide mixture and the odor of stale urine and dog odors was eliminated

EXAMPLE 7

Preparation of a Zeolite/Imide Mixture

The following zeolites and imides were mixed in the ratio indicated and then tested against odors as in Examples 1–7. Results were as recorded in Table 2 below.

TABLE 2

| zeolite | Imide | ratio* | smell control |
|---|---|---|---|
| zeolite 4A | polysuccinimide | 1:1 | Yes |
|  |  | 10:1 | Yes |
|  |  | 50:1 | Yes |
| Sodalite | polysuccinimide | 50:1 | Yes |
| Faujasite | polysuccinimide | 10:1 | Yes |
| Chabazite | polysuccinimide | 10:1 | Yes |
| Lysine | copolymer of polysuccinimide | 10:1 | Yes |
| Mordenite | polysuccinimide | 50:1 | Yes |
| zeolite Y | polysuccinimide | 50:1 | Yes |
| zeolite P | polysuccinimide | 50:1 | Yes |
| zeolite ZSM-5 | polysuccinimide | 50:1 | Yes |
| zeolite 5A | polysuccinimide | 50:1 | Yes |

*ratio = zeolite to imide

EXAMPLE 8

Removal of Human Urine

A sample of human urine (5 mL) was placed on polysuccinimide (0.4 g). No ammonia smell was present and the odor was much milder. The odor was not a urine odor but did have a distinct smell.

When polysuccinimide (0.4 g) alone was used on one day old human urine (20 mL), the odor was decreased substantially and all amine/ammonia odors were removed. There remained an odor, which was not characteristic of urine, but which was noxious, nevertheless.

When zeolite 4A (24 g) alone was used on one day old human urine (5 mL), the odor was decreased substantially and all ammonia odors were removed. There remained an odor, which was not characteristic of urine, but which was noxious, nevertheless and retained some of the amine character.

When a sample of human urine was placed on the zeolite/imide mixture (zeolite 4A/lysine copolymer of polysuccinimide), no odor was detected.

EXAMPLE 9

Removal of Fish Odors

After handling shrimp and crabs, the odor on the hands was noted. When the hands were washed with soap and water, a slight decrease in odor was noted. When lemon juice was placed on the hands a slight decrease in odor was noted. When a zeolite P/polysuccinimide mixture (90:10) was rubbed on the hands the odor was reduced markedly, with only a faint trace of smell noted. When the zeolite P/polysuccinimide mixture was sprinkled lightly on fresh crab and shrimp shells the odor went from an extreme and overpowering fish smell to no odor.

When polysuccinimide was placed in contact with fish juice, the ammonia/amine (fishy) odor was immediately removed. However, there remained a noxious odor, which one would not associate with fish.

EXAMPLE 10

Particle Size

A sample of natural clinoptilolite from a dust collector were separated into sizes of chips (0.5 to 2 mm diameter), grains (0.044 to 0.5 mm diameter) and powder of particles (less than 0.044 mm diameter). These materials were mixed with polysuccinimide (10:1; 10:4; 10:1 zeolite to imide by weight) and then each was tested for odor removal. Odors were removed much quicker by the powder than by the grains and much quicker yet than by the chips. When compared with particle sizes larger than this, it was found that the correlation held that the larger the particle size, the slower the uptake of the odor.

EXAMPLE 11

Removal of Animal Vomit

A sick child threw up stomach juices on a carpet which was treated with a mixture of clinoptilolite and polysuccinimide (97.5:2.5) and allowed to dry overnight and then vacuumed. The odor was immediately eliminated.

A cat threw up a fur ball along with odiferous stomach juices. After removal of the bulk items the wet area was covered with this mixture and the odor was immediately eliminated.

EXAMPLE 12

Removal of Odors from Plastics

The interior of a plastic trash can which had an obnoxious odor was lightly sprinkled with a zeolite P/polysuccinimide mixture. The odor was gone immediately and the plastic container remained free of odor after the mixture was washed out.

EXAMPLE 13

Removal of Odors from Onion

After choping an onion, a mixture of zeolite P and polysuccinimide (90:10) was rubbed on the hands and then washed with a handsoap and water. The odor was significantly lessened.

A piece of onion was then crushed with a spoon and a pungent odor characteristic of onion was expressed. The onion was covered with mixture and the odor was eliminated.

EXAMPLE 14

Removal of Dog Odor

A dog cushion was treated with a mixture of an clinoptilolite/polysuccinimide (95:5) and the dog odor was immediately eliminated. The pillow was then washed and the pillow had the fresh smell of a newly laundered item.

It will be apparent to those skilled in the art that other examples and embodiments of the invention described herein may be utilized without departing from the spirit and scope of the invention, as set forth in the appended claims.

We claim:

1. A composition for reducing odors comprising an effective odor reducing amount of a mixture of a zeolite and an imide.

2. The composition of claim 1 wherein the zeolite and the imide are present in the mixture in a ratio ranging from 1:1 to 99.9:0.1.

3. The composition of claim 1 wherein said zeolite is chabazite.

4. The composition of claim 1 wherein said zeolite is zeolite P.

5. The composition claim 1 wherein said zeolite is zeolite 4A.

6. The composition of claim 1 wherein said zeolite is clinoptilolite.

7. The composition of claim 1 wherein said zeolite has a particle size of less than 0.5 mm diameter.

8. The composition of claim 1 wherein said zeolite has a particle size of less than 0.1 mm diameter.

9. The composition of claim 1 herein said zeolite has a particle size of less than 0.044 mm diameter.

10. The composition of claim 1 wherein said imide is a polyimide.

11. The composition of claim 10 wherein the polyimide is selected from the group of consisting of polysuccinimide, copolymers of polysuccinimide, terpolymers of polysuccinimide, polyglutarimide, copolymers of polyglutarimide, terpolymers of polyglutarimide and combinations thereof.

12. The composition of claim 11 wherein said polyimide is polysuccinimide.

13. The composition of claim 11 wherein said polyimide is a copolymer of polysuccinimide.

14. A method for reducing odor comprising contacting said odor with an effective odor reducing amount of a mixture comprise a zeolite and an imide.

15. The method of claim 14 wherein said zeolite is chabazite.

16. The method of claim 14 wherein said zeolite is zeolite P.

17. The method of claim 14 wherein said zeolite is zeolite 4A.

18. The method of claim 14 wherein said zeolite is clinoptilolite.

19. The method of claim 1 wherein said zeolite has a particle size of less than 0.5 mm diameter.

20. The method of claim 19 wherein said zeolite has a particle size of less than 0.1 mm diameter.

21. The method of claim 19 wherein said zeolite has a particle size of less than 0.044 mm diameter.

22. The method of claim 14 wherein said imide is a polyamide.

23. The method of claim 22 wherein said polyamide is selected from the group of imides consisting of polysuccinimide, copolymers of polysuccinimide, terpolymers of polysuccinimide, terpolymers of polyglutarimide and combinations thereof.

24. The method of claim 23 wherein said polyimide is polysuccinimide.

25. The method of claim 23 wherein said polyimide is a copolymer of polysuccinimide.

26. The method of claim 14 wherein the mixture is dispersed over the site of the odor.

27. The method of claim 25 wherein the site of the odor is on an animal.

* * * * *